US 007635494B2

(12) United States Patent
Chauhan et al.

(10) Patent No.: US 7,635,494 B2
(45) Date of Patent: Dec. 22, 2009

(54) HERBAL COMPOSITION FOR INFLAMMATORY DISORDERS

(75) Inventors: Vijay Chauhan, Mumbai (IN); Ashish Suthar, Mumbai (IN); Dhananjay Sapre, Mumbai (IN); Swati Bal-Tembe, Mumbai (IN); Ashok Kumar Gangopadhyay, Mumbai (IN); Asha Kulkarni-Almeida, Mumbai (IN); Sapna Hasit Parikh, Mumbai (IN); Ravindra Dattatraya Gupte, Mumbai (IN); Nilesh Madhukar Dagia, Mumbai (IN); Somesh Sharma, Mumbai (IN); Shruta Sudheer Dadarkar, Mumbai (IN); Mahesh Gundaji Jadhav, Mumbai (IN); Aditi Amol Tannu, Mumbai (IN)

(73) Assignee: Piramal Life Sciences Limited, Maharashtra (IN)

( * ) Notice: Subject to any disclaimer, the term of this patent is extended or adjusted under 35 U.S.C. 154(b) by 42 days.

(21) Appl. No.: 12/079,853

(22) Filed: Mar. 28, 2008

(65) Prior Publication Data

US 2008/0254157 A1 Oct. 16, 2008

Related U.S. Application Data

(63) Continuation-in-part of application No. PCT/IB2006/053540, filed on Sep. 28, 2006.

(60) Provisional application No. 60/736,443, filed on Nov. 14, 2005.

(30) Foreign Application Priority Data

Sep. 30, 2005 (IN) ...................... 1226/MUM/2005

(51) Int. Cl.
*A01N 65/00* (2009.01)
(52) U.S. Cl. ..................................................... 424/725
(58) Field of Classification Search ........................ None
See application file for complete search history.

(56) References Cited

FOREIGN PATENT DOCUMENTS

WO    WO 2006/016228 A2    2/2006

OTHER PUBLICATIONS

Babu, M.R. et al. "Immunostimulant Profile of a Polyherbal Formulation RV08", Indian Journal of Pharmacology 2001, v. 33, pp. 454-455.
Shekhani, M.S. et al. "An Immunostimulant Sesquiterpene Glycoside From *Sphaeranthus indicus*", Phytochemistry, vol. 28, No. 8, 1990, pp. 2573-2576.
Bafna, A.R. et al. "Actividad immunomoduladora del extracto de methanol de la cabeza floral de *Sphaeranthus indicus* Linn: Immunomodulatory activiry of methanol extract of flower-heads of *Sphaeranthus indicus* Linn", Ars Pharmaceutica, vol. 45, No. 3, 2004, pp. 281-291.
Jain, A. et al. "Inhibition of *Propionibacterium acnes*-induced mediators of inflammation by Indian herbs", Phytomedicine, vol. 10, 2003, pp. 34-38.
Gogte, M.G. et al. "Some Interesting Sesquiterpenoids from *Sphaeranthus indicus* Linn (Composite)", Indian Journal of Chemistry, vol. 25B, Mar. 1986, pp. 233-238.
Sohoni, Jayant S. et al. "A New Eudesmenolide and 2-Hydroxycostic Acid from *Sphaeranthus indicus* Linn. X-ray Molecular Structure of $4_\alpha$, $5_\alpha$-Epoxy-$7_\alpha$-hydroxyeudesmanolide", J. Chem. Soc., 1988, pp. 157-160.
Rahman, A. et al. "7-Hydroxyfrullanolide, an Antimicrobial Sesquiterpene Lactone from *Sphaeranthus indicus* Linn", J. Chem. Research, 1989, pp. 0501-0510.
Jansky, L. et al. "Dynamics of Cytokine Production in Human Peripheral Blood Mononuclear Cells Stimulated by LPS or Infected by *Borrelia*", Physiol. Res., vol. 52, 2003, pp. 593-598.
Brennan, F. M. et al. "Inhibitory Effect of $TNF_\alpha$ Antibodies on Synovial Cell Interleukin-1 Production in Rheumatoid Arthhritis", The Lancet, Jul. 29, 1989, pp. 244-247.
Yamaguchi, Masahiko et al. "Selective Inhibition of Vascular Cell Adhesion Molecule-1 Expression by Verapamil in Human Vascular Endothelial Cells", Transplantation, vol. 63, No. 5, Mar. 15, 1997, pp. 759-764.
Gupta, H. et al. "Inhibition of Lipopolysaccharide-Induced Inflammatory Response by an Apolipoprotein A1 Mimetic Peptide", Circulation Research Journal of the American Heart Association, Aug. 5, 2005, pp. 235-243.
Fukuda, Tetsuko et al. "A novel dual regulator of tumor necrosis factor-$\alpha$ and interleukin-10 protects mice from endotoxin-induced shock", European Journal of Pharmacology, vol. 391, 2000, pp. 317-320.
Mabley, J.G. et al. "Inosine reduces inflammation and improves survival in a murine model of colitis", Am J. Physiol Gastrointest Liver Physiol, vol. 284, Aug. 28, 2002, pp. G138-G144.
Deguchi, Yasuyuki et al. "Curcumin Prevents the Development of Dextran Sulfate Sodium (DSS)-Induced Experimental Colitis", Dig. Dis. Sci, vol. 52, 2007, pp. 2993-2998.
Dieleman, L.A. et al. "Chronic experimental colitis induced by dextran sulphate sodium (DSS) is characterized by Th1 and Th2 cytokines", Clin. Exp. Immunol., vol. 114, 1998, pp. 385-391.

*Primary Examiner*—Michael V Meller
(74) *Attorney, Agent, or Firm*—Hamre, Schumann, Mueller & Larson, P.C.

(57) ABSTRACT

This invention relates to a novel herbal composition comprising an extract of flowering and fruiting heads of the plant, *Sphaeranthus indicus*. The said extract of *Sphaeranthus indicus* contains a compound, 3a-hydroxy-5a,9-dimethyl-3-methylene-3a,4,5,5a,6,7,8,9b-octahydro-3H-naphtho[1,2-b]furan-2-one (7-Hydroxy-4,11(13)-eudesmadien-12,6-olide) (compound 1), as a bioactive marker. The invention also relates to a composition comprising 3a-hydroxy-5a,9-dimethyl-3-methylene-3a,4,5,5a,6,7,8,9b-octahydro-3H-naphtho[1,2-b]furan-2-one (compound 1) as an active ingredient. The invention also relates to methods of manufacture of the said compositions. The invention also relates to methods of administration of the said compositions to a subject in need of treatment for an inflammatory disorder. The invention also relates to tumor necrosis factor-$\alpha$ (TNF-$\alpha$) and interleukin (IL-1, IL-6, IL-8) inhibitory activity of the said compositions. The invention relates to inhibition of the expression of intercellular adhesion molecule 1 (ICAM-1), vascular-cell adhesion molecule 1 (VCAM-1), and E-Selectin by the said compositions. The said compositions may optionally contain at least one anti-inflammatory agent or can be used in combination with at least one anti-inflammatory agent.

8 Claims, 7 Drawing Sheets

N: Naïve mice

D: DSS-fed mice

P: Prednisolone treated (5 mg/kg, o.i.d, p.o.; on day 3, 6 and 10) DSS-fed mice

E: Extract of example 1 treated (400 mg/kg, p.o; on day 3, 6 and 10), DSS-fed mice

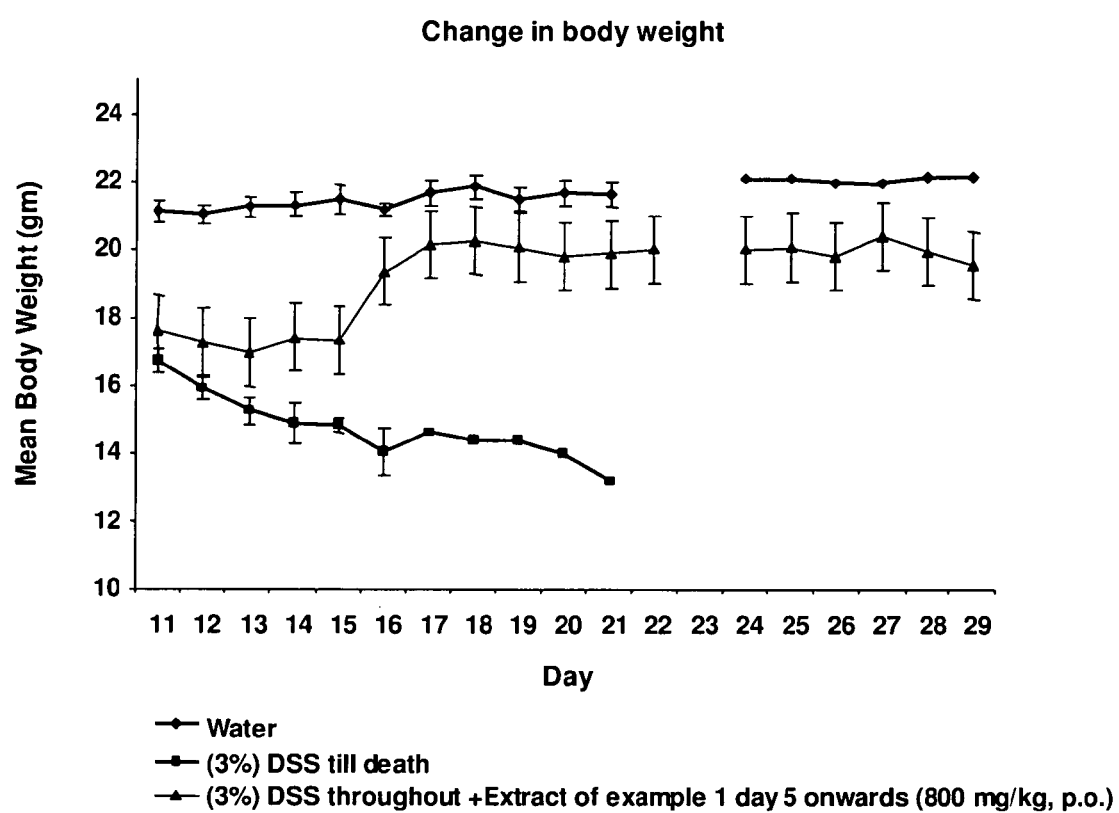

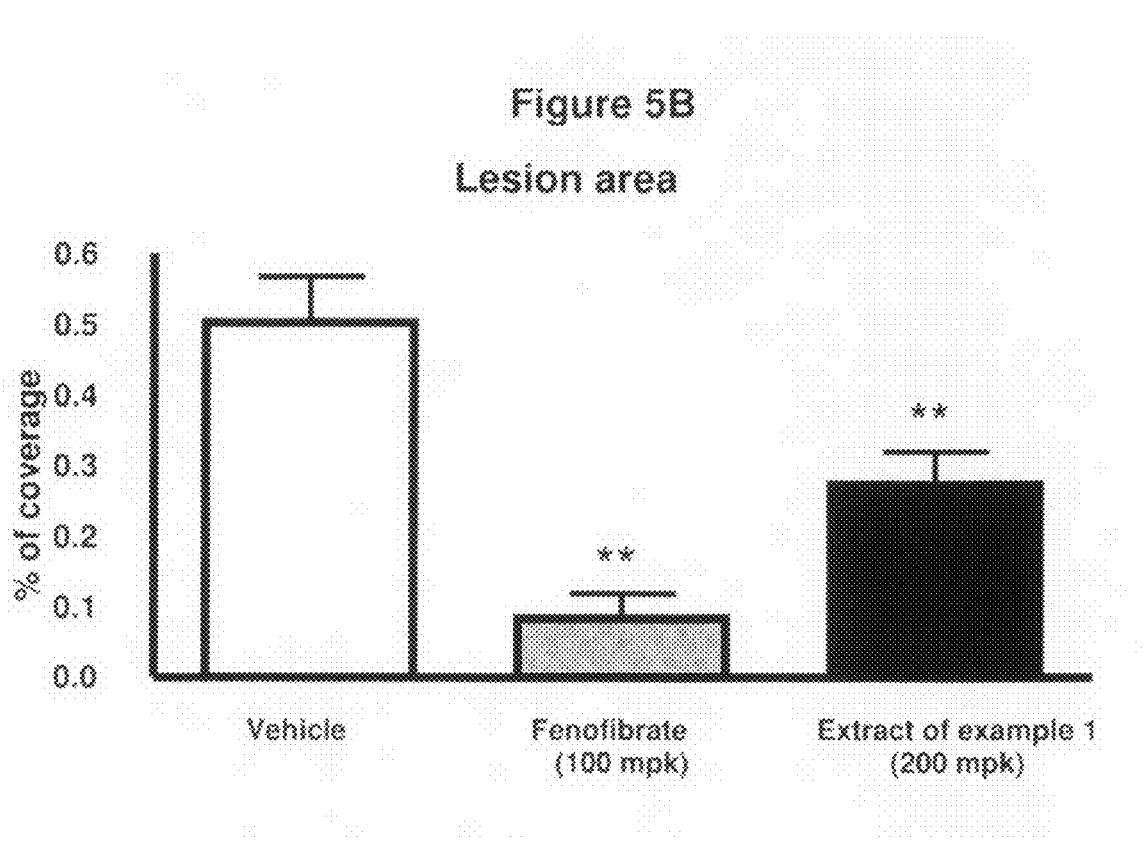

HERBAL COMPOSITION FOR INFLAMMATORY DISORDERS

FIELD OF THE INVENTION

The present invention relates to a novel herbal composition comprising an extract of flowering and fruiting heads of a plant, *Sphaeranthus indicus*. The present invention further relates to a herbal composition containing an extract obtained from the flowering and fruiting heads of *Sphaeranthus indicus*, comprising a compound, 3a-hydroxy-5a,9-dimethyl-3-methylene-3a,4,5,5a,6,7,8,9b-octahydro-3H-naphtho[1,2-b]furan-2-one (7-Hydroxy-4,11(13)-eudesmadien-12,6-olide) (compound 1) as a bioactive marker, and optionally other active(s) for the effective treatment of inflammatory disorders. The present invention also relates to a pharmaceutical composition comprising 3a-hydroxy-5a,9-dimethyl-3-methylene-3a,4,5,5a,6,7,8,9b-octahydro-3H-naphtho[1,2-b]furan-2-one (compound 1) as an active ingredient and pharmaceutically acceptable carriers, for use in the treatment of inflammatory disorders. The present invention also relates to a method of manufacture of the said compositions. The said compositions of the present inventions are adapted for the treatment of inflammatory disorders. The invention also relates to tumor necrosis factor-α (TNF-α) and interleukin (IL-1, IL-6, IL-8) inhibitory activity of the said compositions. The present invention further relates to inhibition of the expression of intercellular adhesion molecule 1 (ICAM-1), vascular-cell adhesion molecule 1 (VCAM-1), and E-Selectin by the said compositions.

The invention also discloses methods of administration of the said compositions for treatment of inflammatory disorders. Optionally, the said extract or composition comprising said extract or composition comprising compound 1 may be used in combination with at least one other anti-inflammatory agent.

BACKGROUND OF THE INVENTION

Inflammation plays a fundamental role in host defenses and the progression of immune-mediated disease. The inflammatory response is initiated in response to injury (e.g. trauma, ischemia, and foreign particles) and infection (e.g. bacterial or viral infection) by multiple events, including chemical mediators (e.g. cytokines and prostaglandins) and inflammatory cells (e.g. leukocytes). It is characterized by increased blood flow to the tissue, causing pyrexia, erythema, induration and pain.

A delicate well-balanced interplay between the humoral and cellular immune elements in the inflammatory response enables the elimination of harmful agents and the initiation of the repair of damaged tissue. When this delicately balanced interplay is disrupted, the inflammatory response may result in considerable damage to normal tissue and may be more harmful than the original insult that initiated the reaction. In these cases of uncontrolled inflammatory responses, clinical intervention is needed to prevent tissue damage and organ dysfunction. Diseases such as rheumatoid arthritis, osteoarthritis, Crohn's disease, asthma, allergies, septic shock syndrome, atherosclerosis, inflammatory bowel disease among other clinical conditions are characterized by chronic inflammation.

Cytokines, especially IL-1β, IL-6, IL-8 and TNF-α, play an important role in the inflammatory process.

TNF-α, a pleiotropic cytokine, is produced mainly by macrophages, but it may be produced by other types of cells also. TNF-α demonstrates beneficial as well as pathological activities. It has both growth stimulating effects and growth inhibitory properties, besides being self-regulatory. The beneficial functions of TNF-α include maintaining homeostasis by regulating the body's circadian rhythm, mounting an immune response to bacterial, viral, fungal and parasitic infections, replacing or remodeling injured tissue by stimulating fibroblast growth and as the name suggests, killing certain tumors.

Although TNF-α plays a critical role in innate and acquired immune responses, inappropriate production of TNF-α can produce pathological changes resulting in chronic inflammation and tissue damage. TNF-α has been shown to play a crucial role in the pathogenesis of many chronic inflammatory disease such as inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis/bone resorption, coronary heart disease, vasculitis, ulcerative colitis, psoriasis, adult respiratory distress syndrome, diabetes, skin delayed type hypersensitivity disorders and Alzheimer's disease. Interleukin-1 (IL-1) is an important part of the innate immune system, which regulates functions of the adaptive immune system. The balance between IL-1 and IL-1 receptor antagonist (IL-1ra) in local tissues influences the possible development of an inflammatory disease and resultant structural damage. In the presence of an excess amount of IL-1, inflammatory and autoimmune disorders may be developed in joints, lungs, gastrointestinal tract, central nervous system (CNS) or blood vessels.

Among various inflammatory disorders, rheumatoid arthritis (RA) is an autoimmune disorder. RA is a chronic, systemic, articular inflammatory disease of unknown etiology. In RA, the normally thin synovial lining of joints is replaced by an inflammatory, highly vascularized, invasive fibrocollagenase tissue (pannus), which is destructive to both cartilage and bone. Areas that may be affected include the joints of the hands, wrists, neck, jaw, elbows, knee, feet and ankles. Cartilage destruction in RA is linked to aberrant cytokines and growth factor expression in the affected joints.

Two clinically important cytokines released in the synovium are IL-1β and TNF-α. TNF-α can upregulate its own expression as well as facilitate the expression of other genes implicated in RA, including IL-1β, IL-6, IL-8, cyclooxygenase-2 (COX-2), inducible nitric oxide synthetase (iNOS), intercellular adhesion molecule 1 (ICAM-1), vascular-cell adhesion molecule 1 (VCAM-1), and E-Selectin. This type of positive regulatory loop may amplify and perpetuate local inflammatory responses. Therefore, the inappropriate or over-expression of TNF-α leads to a coordinated increase in the expression of many genes whose products mediate inflammatory and immune responses and thereby lead to the clinical manifestations of RA.

The recruitment and retention of leukocytes is a critical event in the pathogenesis of all chronic inflammatory disorders including RA. Moreover, the adhesion of circulating leukocytes, especially monocytes, to vascular endothelium is also a crucial event in the development of atherosclerosis. This process depends on the interaction between the adhesion molecules expressed on the surface of endothelial cells such as ICAM-1, VCAM-1, and E-Selectin and their cognate ligands on leukocytes. Hence, ICAM-1, VCAM-1, and E-Selectin are responsible for the recruitment of inflammatory cells, such as neutrophils, eosinophils, and T lymphocytes, from the circulation to the site of inflammation. These adhesion proteins are normally at low level on the endothelial cell surface but are greatly induced by various proinflammatory cytokines such as TNF-α.

Another inflammatory disorder, inflammatory bowel disease (IBD) is a group of disorders that cause the inflammation of the intestines. The inflammation lasts for a long time and usually relapses. The two major types of IBD disorders are Crohn's disease and ulcerative colitis.

Crohn's disease occurs when the lining and wall of the intestines becomes inflamed resulting in the development of ulcers. Although Crohn's disease can occur in any part of the digestive system, it often occurs in the lower part of the small intestine where it joins the colon.

Ulcerative colitis is a chronic inflammatory disease of unknown etiology afflicting the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Signs and symptoms of the disease include cramping, lower abdominal pain, rectal bleeding, and frequent, loose discharges consisting mainly of blood, pus, and mucus with scanty fecal particles. A total colectomy may be required for acute, severe or chronic, unremitting ulcerative colitis.

Yet another inflammatory disorder is atherosclerosis. Atherosclerosis is a disease affecting arterial blood vessels. It is a chronic inflammatory response in the walls of arteries, in large part due to the deposition of lipoproteins (plasma proteins that carry cholesterol and triglycerides). It is commonly referred to as "hardening" or "furring" of the arteries. It is caused by the formation of multiple plaques within the arteries resulting in the inflammation of the arteries.

The most common therapy for treatment of inflammatory disorders involves use of non-steroidal anti-inflammatory drugs (NSAIDs) e.g. naproxen, diclofenac, ibuprofen to alleviate symptoms such as pain. However, despite the widespread use of NSAIDs, many individuals cannot tolerate the doses necessary to treat the disorder over a prolonged period of time as NSAIDs are known to cause gastric erosions. Moreover, NSAIDs merely treat the symptoms of disorder and not the cause.

When patients fail to respond to NSAIDs, other drugs such as methotrexate, gold salts, D-penicillamine and corticosteroids are used. These drugs also have significant toxic effects. Monoclonal antibody drugs such as infliximab, etanercept and adalimumab are useful as anti-inflammatory agents, but have drawbacks such as route of administration (only parenteral), high cost, allergy induction, activation of latent tuberculosis, increased risk of cancer and congestive heart disease.

Hence, there is a need for the development of improved and alternative medicaments with reduced side effects for the prevention and treatment of inflammatory disorders caused by increased IL-1 and TNF-α.

Herbs have been known and used throughout the world for treatment of many conditions. There is evidence that products derived from plants have potential pharmacological and therapeutic effects on mammals and tend to have less deleterious side effects than synthetic drugs.

The present invention describes a novel herbal composition, which comprises extract of flowering and fruiting heads of the plant, *Sphaeranthus indicus*. The composition can be used for treatment of various inflammatory disorders with minimal side effects. *Sphaeranthus indicus* is a common weed found in rice fields. It belongs to the family Asteraceae and in the literature of Ayurveda, it is known as mahamundi or gorakhmundi. The plant, available throughout India, is a branched herb with purple flowers. It is used in hepatic and gastric disorders. It is used in folk medicine as a remedy for various ailments including dysentery, pain in the uterus and vagina, diseases of the chest, purification and enrichment of blood, urinary tract infections, wound healing and several other diseases. A polyherbal formulation "RV-08", containing *Sphaeranthus indicus* has been developed with a view to counteract immunodeficient disorders (Indian Journal of Pharmacology, 33, 454-55, (2001)). Isolation of a new sesquiterpene glycoside, sphaeranthanolide, from the flowers of *Sphaeranthus indicus* has been reported. The isolated compound, Sphaeranthanolide, exhibited immunostimulating activity. (Phytochemistry, 29 (8), 2573-76, (1990)).

Immunomodulatory activity of methanol extract of flowerheads of *Sphaeranthus indicus* has been reported (Ars Pharmaceutica 45:3; 281-91, (2004)).

The aqueous extract obtained from roots of *Sphaeranthus indicus* is reported to be moderately active in down-regulating *Propionibacterium acnes* induced TNF-α and IL-8 production. *Sphaeranthus indicus* caused a smaller, still significant suppression of reactive oxygen species (Phytomedicine, 10 (1), 34-38, (2003)).

To our knowledge, there is no report of any medicament containing extract of flowering and fruiting heads of *Sphaeranthus indicus* for treatment of inflammatory disorders. To overcome the problems of side effects of present line of treatment, such as allergy induction, activation of latent tuberculosis, myelosuppression, increased risk of cancer and congestive heart disease, associated with the prior art compositions, the present inventors have prepared a novel herbal composition effective against inflammation, having inhibitory activity against TNF-α, interleukins (IL-1, IL-6, IL-8) and the expression of intercellular adhesion molecule 1 (ICAM-1), vascular-cell adhesion molecule 1 (VCAM-1), and E-Selectin. The compositions of the present invention can also be used in combination with at least one other anti-inflammatory agent.

OBJECTS OF THE INVENTION

An object of the present invention is directed at providing a novel herbal composition comprising a therapeutically effective amount of an extract of flowering and fruiting heads of *Sphaeranthus indicus* as an active ingredient along with pharmaceutically acceptable carriers.

Another object of the present invention is to provide a composition comprising a therapeutically effective amount of 3a-hydroxy-5a,9-dimethyl-3-methylene-3a,4,5,5a,6,7,8,9b-octahydro-3H-naphtho[1,2-b]furan-2-one (compound 1) as an active ingredient along with pharmaceutically acceptable carriers, for the treatment of inflammatory disorders.

Another further object of the present invention is to provide a method of manufacture of the said compositions.

Yet another further object of the present invention is to provide a composition comprising a therapeutically effective amount of the active ingredient selected from either the extract of *Sphaeranthus indicus* or the compound 1 for the treatment of disorders mediated by TNF-α and interleukins (IL-1, IL-6, IL-8).

Yet another further object of the present invention is to provide a composition comprising a therapeutically effective amount of the active ingredient selected from either the extract of *Sphaeranthus indicus* or the compound 1, for the treatment of disorders mediated by intercellular adhesion molecule 1 (ICAM-1), vascular-cell adhesion molecule 1 (VCAM-1), and E-Selectin.

Another object of the present invention is to provide a composition comprising a therapeutically effective amount of the active ingredient selected from either the extract of *Sphaeranthus indicus* or the compound 1 for the treatment of inflammatory disorders.

Yet another object of the present invention is to provide a composition comprising a therapeutically effective amount of the active ingredient selected from either the extract of *Sphaeranthus indicus* or the compound 1, to treat inflammatory disorders mediated by TNF-α.

Yet another object of the present invention is to provide a composition comprising a therapeutically effective amount of the active ingredient selected from either the extract of *Sphaeranthus indicus* or the compound 1, to treat inflammatory disorders mediated by interleukins (IL-1, IL-6, IL-8).

Yet another object of the present invention is to provide a composition comprising a therapeutically effective amount of the active ingredient selected from either the extract of *Sphaeranthus indicus* or the compound 1, to treat inflammatory disorders mediated by intercellular adhesion molecule 1 (ICAM-1), vascular-cell adhesion molecule 1 (VCAM-1), and E-Selectin.

Yet another objective of the present invention is to provide a composition comprising a therapeutically effective amount of the active ingredient selected from either the extract of *Sphaeranthus indicus* or the compound 1 in combination with at least one bioactive substance to obtain a synergistic effect.

Yet another objective of the invention is to provide the use of said compositions alone or in combination with at least one other anti-inflammatory agent to treat inflammatory disorders including rheumatoid arthritis.

Other objects and further scope of applicability of the present invention will become apparent from the detailed description to follow.

SUMMARY OF THE INVENTION

Thus according to one aspect of the present invention, there is provided a novel herbal composition comprising a therapeutically effective amount of an extract of flowering and fruiting heads of *Sphaeranthus indicus* as an active ingredient along with pharmaceutically acceptable carriers.

According to another aspect of the present invention, there is provided a composition comprising a therapeutically effective amount of 3a-hydroxy-5a,9-dimethyl-3-methylene-3a,4, 5,5a,6,7,8,9b-octahydro-3H-naphtho[1,2-b]furan-2-one (compound 1) as an active ingredient along with pharmaceutically acceptable carriers, for the treatment of inflammatory disorders.

According to a further aspect of the present invention, there is provided a method of manufacture of the said compositions.

According to another further aspect of the present invention, there is provided a composition comprising a therapeutically effective amount of the active ingredient selected from either the extract of *Sphaeranthus indicus* or the compound 1 for the treatment of disorders mediated by TNF-α and interleukins (IL-1, IL-6, IL-8). According to another further aspect of the present invention, there is provided a composition comprising a therapeutically effective amount of the active ingredient selected from either the extract of *Sphaeranthus indicus* or the compound 1, for the treatment of disorders mediated by intercellular adhesion molecule 1 (ICAM-1), vascular-cell adhesion molecule 1 (VCAM-1), and E-Selectin.

According to further aspect of the present invention, there is provided a composition comprising a therapeutically effective amount of the active ingredient selected from either the extract of *Sphaeranthus indicus* or the compound 1 for the treatment of inflammatory disorders.

According to further aspect of the present invention, there is provided a composition comprising a therapeutically effective amount of the active ingredient selected from either the extract of *Sphaeranthus indicus* or the compound 1, to treat inflammatory disorders mediated by TNF-α.

According to further aspect of the present invention, there is provided a composition comprising a therapeutically effective amount of the active ingredient selected from either the extract of *Sphaeranthus indicus* or the compound 1, to treat inflammatory disorders mediated by interleukins (IL-1, IL-6, IL-8). According to further aspect of the present invention, there is provided a composition comprising a therapeutically effective amount of the active ingredient selected from either the extract of *Sphaeranthus indicus* or the compound 1, to treat inflammatory disorders mediated by intercellular adhesion molecule 1 (ICAM-1), vascular-cell adhesion molecule 1 (VCAM-1), and E-Selectin.

According to another further aspect of the present invention, there is provided a composition comprising a therapeutically effective amount of the active ingredient selected from either the extract of *Sphaeranthus indicus* or the compound 1 in combination with at least one bioactive substance to obtain a synergistic effect.

Effect on DSS-induced weight loss (%), rectal bleeding, stool consistency, disease activity index and colon length in C57BL/6J mice is indicated. Prednisolone was used as standard.

Figure 2:
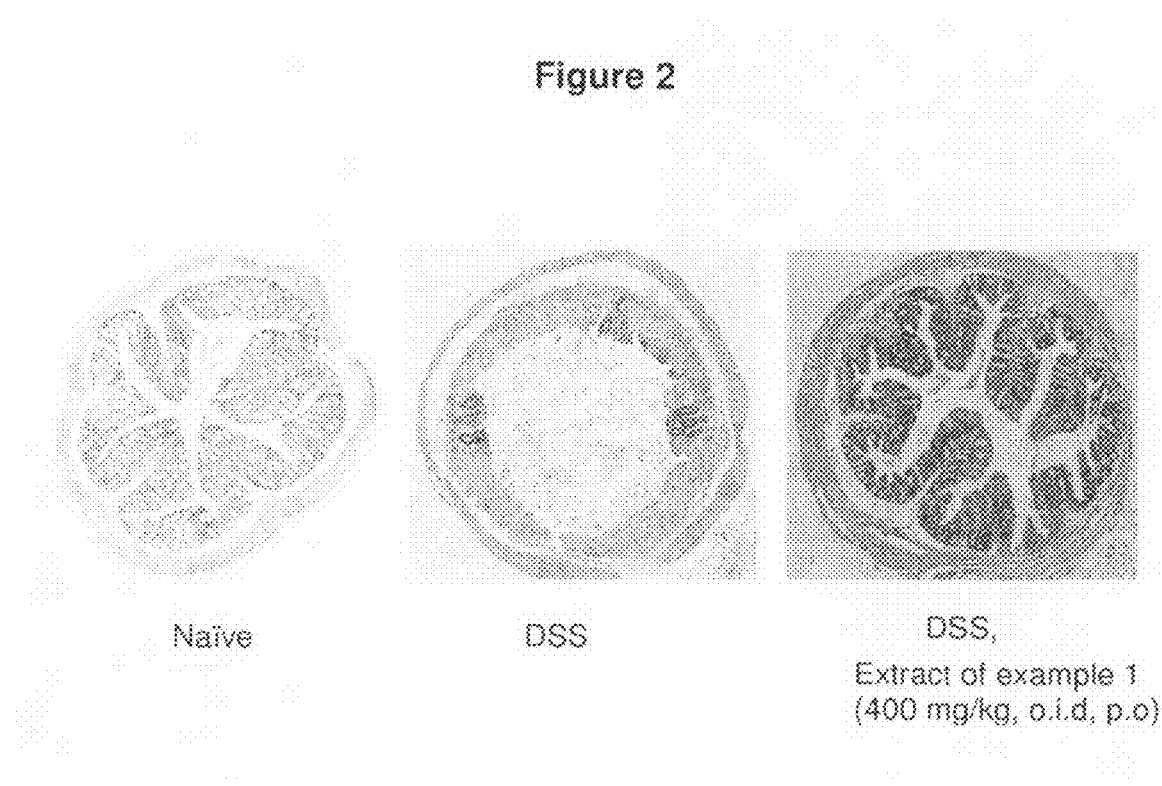

FIG. 2: Effect of extract of example 1 (fed coincident with DSS treatment) on histological abnormalities in C57BL/6J mice.

Effect on DSS-induced histological abnormalities is indicated.

Figure 3:
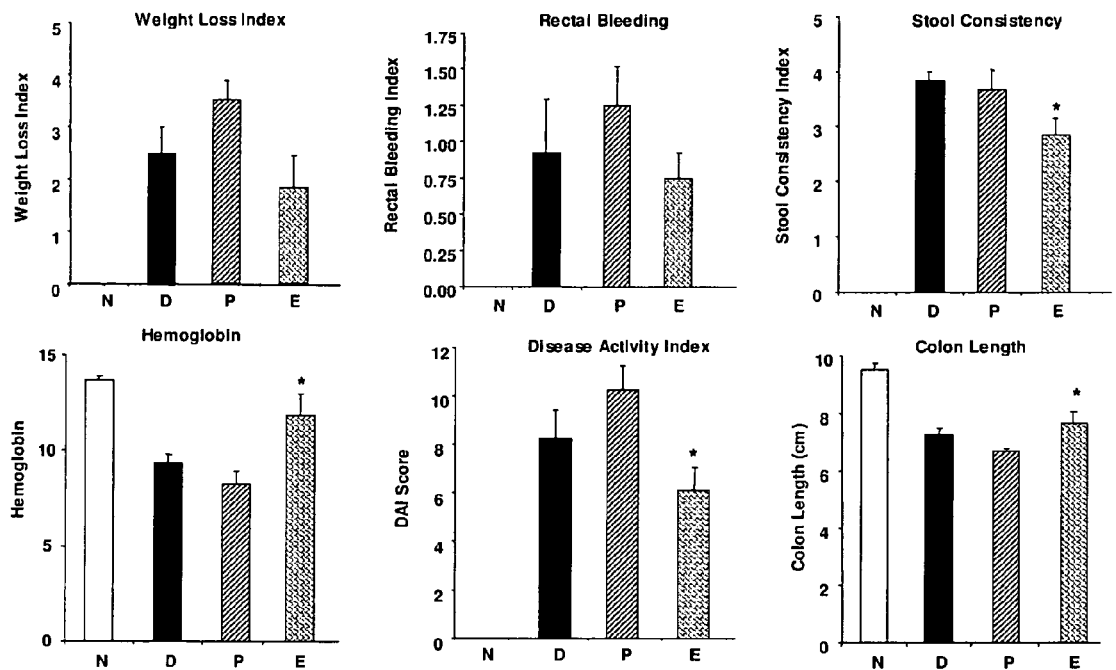

FIG. 3: Effect of extract of example 1 (fed after DSS-induced disease expression) in C57BL/6J mice.

Effect on DSS-induced weight loss (%), rectal bleeding, stool consistency, haemoglobin, disease activity index and colon length in C57BL/6J mice is indicated. Prednisolone was used as standard.

FIG. 4A: Effect of example 1 (fed after DSS treatment) in C57BL/6J mice.

Effect on DSS-induced weight loss in C57BL/6J mice is indicated.

Figure 4B:
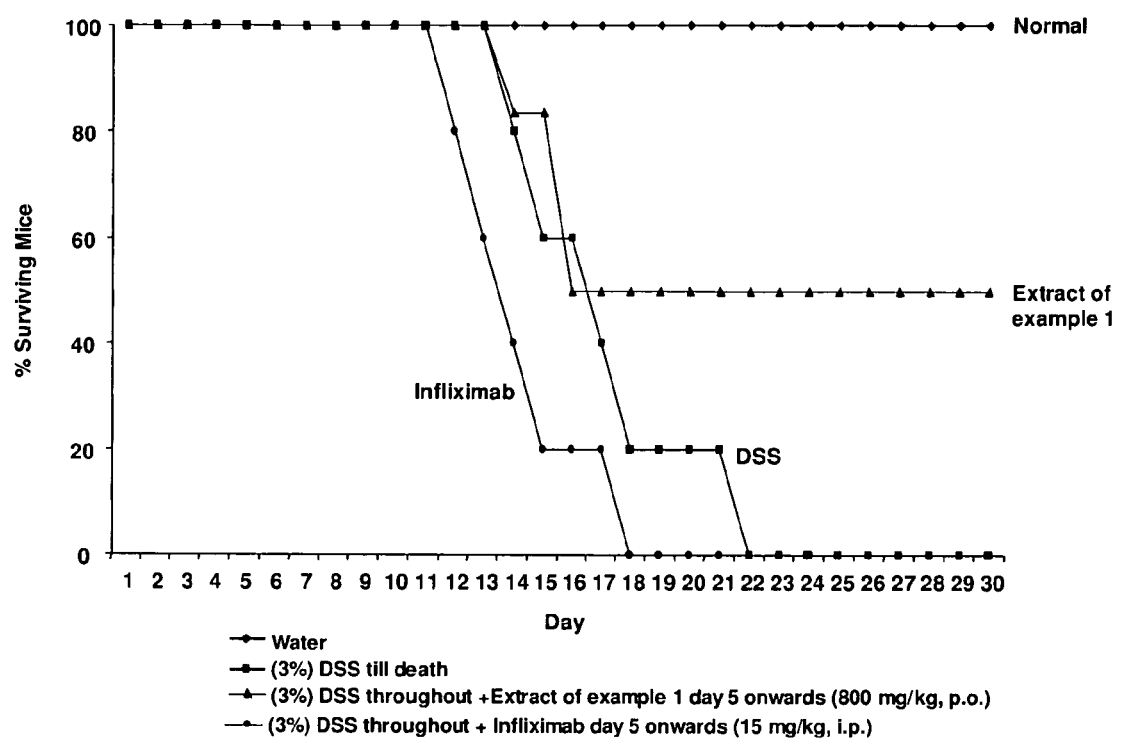

FIG. 4B: Effect of extract of example 1 on survival of C57BL/6J mice.

Effect on survival of mice against DSS-induced colitic death is indicated

Figure 5A:
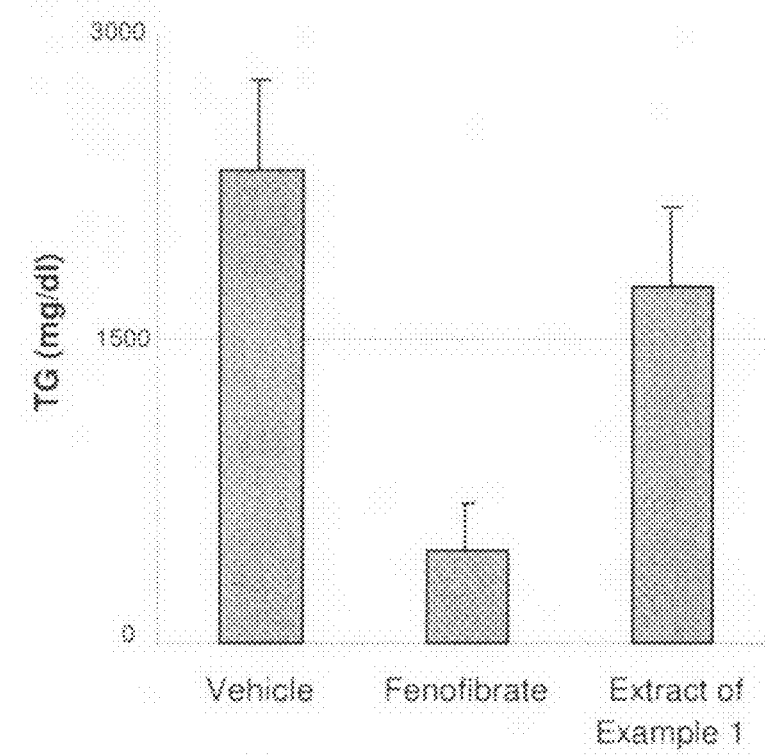

FIG. 5A: Effect of extract of example 1 on triglyceride levels (TG) in fat-fed hyperlipidemic hamsters.

Effect on triglyceride levels in fat-fed hyperlipidemic hamsters is indicated. Fenofibrate was used as a standard.

FIG. 5B: Effect of extract of example 1 on atherosclerosis progression in fat-fed hyperlipidemic hamsters.

Effect on atherosclerosis progression in fat-fed hyperlipidemic hamsters is indicated. Fenofibrate was used as a standard.

DETAILED DESCRIPTION OF THE INVENTION

It should be understood that the detailed description and specific examples, while indicating embodiments of the invention, are given by way of illustration only, since various changes and modifications within the spirit and scope of the invention will become apparent to those skilled in the art. One skilled in the art, based upon the description herein, may utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs.

The term "inflammatory disorder" as used herein refers to a disease or a condition characterized by chronic inflammation including but not limited to rheumatoid arthritis, osteoarthritis, juvenile rheumatoid arthritis, psoriatic arthritis, refractory rheumatoid arthritis, chronic non-rheumatoid arthritis, osteoporosis/bone resorption, coronary heart disease, atherosclerosis, vasculitis, ulcerative colitis, psoriasis, Crohn's disease, adult respiratory distress syndrome, skin delayed type hypersensitivity disorders, septic shock syndrome and inflammatory bowel disease.

The term "pharmaceutically acceptable" as used herein means the carrier, diluent, excipients, and/or salt must be compatible with the other ingredients of the formulation, and not deleterious to the recipient thereof.

The term "pharmaceutically acceptable carrier" as used herein means a non-toxic, inert solid, semi-solid, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

The term, "therapeutically effective amount" as used herein means an amount of compound or composition (e.g., the Sphaeranthus indicus extract) sufficient to significantly induce a positive modification in the condition to be regulated or treated, but low enough to avoid side effects if any (at a reasonable benefit/risk ratio), within the scope of sound medical judgment. The therapeutically effective amount of the compound or composition will vary with the particular condition being treated, the age and physical condition of the end user, the severity of the condition being treated/prevented, the duration of the treatment, the nature of concurrent therapy, the specific compound or composition employed, the particular pharmaceutically acceptable carrier utilized, and like factors. As used herein, all percentages are by weight unless otherwise specified.

The term "bioactive marker" is used herein to define a characteristic (or a phytochemical profile) which is correlated with an acceptable degree of pharmaceutical activity.

The "maximum practicable dose" is the largest amount of a drug that an adult can take with safety.

It should be noted that, as used in the specification and the appended claims, the singular forms "a," "an," and "the" include plural referents unless the content clearly dictates otherwise.

"Sphaeranthus indicus extract" or "an extract of Sphaeranthus indicus", mentioned herein means a blend of compounds present in the plant Sphaeranthus indicus. Such compounds are extracted from the dried flowering and fruiting heads of the plant using extraction procedures well known in the art (e.g., the use of organic solvents such as lower alcohols, alkyl esters, alkyl ethers, alkyl ketones, chloroform, petroleum ether, hexane and/or inorganic solvents such as water). The present process for extraction of phytoconstituent derivatives from flowering and fruiting heads of Sphaeranthus indicus can be scaled up for large-scale preparation.

The term "active ingredient" as used herein refers to "Sphaeranthus indicus extract" or "the compound 1" or "an enriched extract of Sphaeranthus indicus containing a mixture of two or more active compounds".

Sphaeranthus indicus extract can be standardized using conventional techniques such as High Performance Liquid Chromatography (HPLC) or High Performance Thin Layer Chromatography (HPTLC).

In an embodiment, the invention provides a herbal composition comprising standardized extract of Sphaeranthus indicus along with pharmaceutically acceptable carriers.

Bioactive marker compounds may be isolated from the extract of flowering and fruiting heads of Sphaeranthus indicus by bioactivity guided column chromatographic purification and preparative HPLC. Compounds may be characterized by analysis of the spectral data.

The herbal composition of the present invention comprises an extract of flowering and fruiting heads of Sphaeranthus indicus, comprising 2-9% of 3a-hydroxy-5a,9-dimethyl-3-methylene-3a,4,5,5a,6,7,8,9b-octahydro-3H-naphtho[1,2-b]furan-2-one (compound 1), as a bioactive marker and optionally other active (s).

In an embodiment, the invention provides a composition comprising 3a-hydroxy-5a,9-dimethyl-3-methylene-3a,4,5,5a,6,7,8,9b-octahydro-3H-naphtho[1,2-b]furan-2-one (compound 1) as an active ingredient, along with pharmaceutically acceptable carriers.

In an embodiment, the invention provides the use of the said composition comprising 3a-hydroxy-5a,9-dimethyl-3-methylene-3a,4,5,5a,6,7,8,9b-octahydro-3H-naphtho[1,2-b]furan-2-one (compound 1), for the manufacture of a medicament for the treatment of inflammatory disorders.

The invention is further directed to a method of manufacturing compositions useful for treating inflammatory disorders. The standardized extract of Sphaeranthus indicus is mixed with pharmaceutically acceptable carriers and formulated into therapeutic dosage forms. The dose to be administered daily is to be selected to suit the desired effect.

In an embodiment the said herbal composition comprising the standardized extract of Sphaeranthus indicus is provided for the treatment of inflammatory disorders.

In another embodiment of the invention, composition comprising 3a-hydroxy-5a,9-dimethyl-3-methylene-3a,4,5,5a,6,7,8,9b-octahydro-3H-naphtho[1,2-b]furan-2-one (compound 1), along with pharmaceutically acceptable carriers, is provided for the treatment of inflammatory disorders.

The compound 1,3a-hydroxy-5a,9-dimethyl-3-methylene-3a,4,5,5a,6,7,8,9b-octahydro-3H-naphtho[1,2-b]furan-2-one, was isolated from the extract of Sphaeranthus indicus by a procedure known in the related art and was characterized by Nuclear Magnetic resonance (NMR) and Mass spectrometry. The composition comprising the compound 1,3a-hydroxy-5a,9-dimethyl-3-methylene-3a,4,5,5a,6,7,8,9b-octahydro-3H-naphtho[1,2-b]furan-2-one, which compound may also be obtained from other plant sources or may be manufactured by conventional synthetic methods known to an artisan skilled in art.

Accordingly present invention encompasses within its scope a pharmaceutical composition comprising compound 1, which may be obtained from other sources, for use in the treatment of inflammatory disorders.

In yet another embodiment of the invention, there is provided a method of manufacturing pharmaceutical composition comprising 3a-hydroxy-5a,9-dimethyl-3-methylene-3a, 4,5,5a,6,7,8,9b-octahydro-3H-naphtho[1,2-b]furan-2-one (compound 1) by mixing the compound 1 with one or more pharmaceutically acceptable carriers and formulating into therapeutic dosage forms. The dose to be administered daily is to be selected to suit the desired effect.

The compositions of the present invention can be administered orally, for example in the form of pills, tablets, coated tablets, capsules, granules, elixirs or syrup.

The extract of flowering and fruiting heads of *Sphaeranthus indicus* is used to prepare oral preparations containing 3-70% by weight of the said extract, which is thoroughly blended into a conventional base as will be hereafter described in detail. The extract of flowering and fruiting heads containing 2-9% (w/w) of compound 1 as bioactive marker, is sufficient to achieve the desired results.

The compound 1, 3a-hydroxy-5a,9-dimethyl-3-methylene-3a,4,5,5a,6,7,8,9b-octahydro-3H-naphtho[1,2-b]furan-2-one, is used to prepare oral preparations containing 3-99% by weight of the said compound, which is thoroughly blended into a conventional base as will be hereafter described in detail.

The compositions of the present invention can be used for topical and transdermal administration. The topical compositions useful in the present invention involve formulations suitable for topical application to skin. The compositions may be formulated into a wide variety of product types that include but are not limited to lotions, creams, gels, sticks, sprays, or ointments.

The extract of flowering and fruiting heads of *Sphaeranthus indicus* is used to prepare topical preparations containing 1-15% by weight of the said extract which is thoroughly blended into a conventional base as will be hereafter described in detail. The extract of flowering and fruiting heads of *Sphaeranthus indicus*, containing approximately 2-9% (w/w) of compound 1 as bioactive marker, is sufficient to achieve the desired results.

In an embodiment the said compositions are provided for the treatment of inflammatory disorders mediated by TNF-α and interleukins (IL-1, IL-6, IL-8).

In an embodiment the said compositions are provided for the treatment of inflammatory disorders mediated by intercellular adhesion molecule 1 (ICAM-1), vascular-cell adhesion molecule 1 (VCAM-1), and E-Selectin.

Actual dosage levels of the active ingredient, "*Sphaeranthus indicus* extract" or the compound 1 in the compositions of this invention may be varied so as to obtain an amount of the active ingredient, which is effective to achieve the desired therapeutic response for a particular patient, composition, and mode of administration.

The selected dosage level will depend upon a variety of factors including the activity of the particular active ingredient, "*Sphaeranthus indicus* extract" or "the compound 1" employed, the route of administration, the time of administration, the rate of excretion of the particular composition being employed, the duration of the treatment, use in combination with the other extracts, the age, sex, weight, condition, general health and prior medical history of the patient being treated, and like factors well known in the medical arts.

In another embodiment, the invention provides a composition comprising the active ingredient, "*Sphaeranthus indicus* extract" or the compound 1, in combination with at least one other herbal extract exhibiting anti-inflammatory activity to obtain a synergistic effect. Such other plant may be selected from plants such as *Curcuma longa* and *Zingiber officinale*.

In yet another embodiment, the composition further comprises the active ingredient, "*Sphaeranthus indicus* extract" or the compound 1, in combination with at least one bioactive substance to obtain a synergistic effect.

In yet another embodiment, the composition of the present invention comprising the active ingredient, "*Sphaeranthus indicus* extract" or the compound 1, may optionally contain at least one other anti-inflammatory agent or can also be used in combination with a conventional anti-inflammatory agent. The anti-inflammatory agent may be selected from steroids such as prednisolone, hydrocortisone; disease modifying antirheumatic drugs (DMARDs) such as methotrexate, sulfasalazine; or NSAIDS such as naproxen, diclofenac, ibuprofen and the like.

In an embodiment, the said herbal composition comprising the active ingredient, "*Sphaeranthus indicus* extract" or the compound 1 isolated from the *Sphaeranthus indicus* extract, is provided for the treatment of rheumatoid arthritis.

In an embodiment, the said herbal composition comprising the active ingredient, "*Sphaeranthus indicus* extract" or the compound 1 isolated from the *Sphaeranthus indicus* extract, is provided for the treatment of inflammatory bowel disease.

In an embodiment, the said herbal composition comprising the active ingredient, "*Sphaeranthus indicus* extract" or the compound 1 isolated from the *Sphaeranthus indicus* extract, is provided for the treatment of ulcerative colitis.

In an embodiment, the said herbal composition comprising the active ingredient, "*Sphaeranthus indicus* extract" or the compound 1 isolated from the *Sphaeranthus indicus* extract, is provided for the treatment of atherosclerosis.

Another embodiment of the present invention also relates to TNF-α and interleukin (IL-1, IL-6, IL-8) inhibitory activity of the compositions comprising the said active ingredient.

Another embodiment of the present invention also relates to inhibition of cell surface expression of adhesion molecules such as intercellular adhesion molecule 1 (ICAM-1), vascular-cell adhesion molecule 1 (VCAM-1), and E-Selectin by the compositions comprising the said active ingredient The compositions of the present invention are suitable for use in the treatment of both acute and chronic forms of inflammatory disorders mediated by TNF-α, interleukins (IL-1, IL-6, IL-8) and ICAM-1, VCAM-1 and E-Selectin, in particular, rheumatoid arthritis, juvenile rheumatoid arthritis, psoriatic arthritis, osteoarthritis, refractory rheumatoid arthritis, chronic non-rheumatoid arthritis, osteoporosis/bone resorption, coronary heart disease, vasculitis, ulcerative colitis, psoriasis, adult respiratory distress syndrome, Alzheimer's disease in humans. Also the compositions of the present invention can be used for treating inflammation in diseases like inflammatory bowel disease, Crohn's disease, septic shock syndrome, atherosclerosis, and various autoimmune diseases among other clinical conditions. The present invention is also related to a method of treating inflammatory disorders comprising the administration of the compositions selectively by oral route, by topical application, by transdermal application.

The following examples illustrate but do not limit the scope of the invention. It is to be understood by those of the ordinary skill in the art that the present discussion is of exemplary embodiments only, and is not intended as limiting the broader aspects of the present invention, which broader aspects are embodied in the exemplary construction.

EXAMPLE 1

Preparation of Methanol Extract of *Sphaeranthus indicus*

Dried flowering and fruiting heads of *Sphaeranthus indicus* (200 g) were pulverized. The powdered material was extracted using methanol (2.5 L) by stirring at 60° C. for 3 hrs. The extract was filtered under vacuum. This extraction process was repeated two more times. The extracts were combined and concentrated.

Yield: 23.29 g (11.65% w/w).

The extract of example 1 was found to contain 6% of compound 1 (described in example 4), as estimated by HPTLC.

EXAMPLE 2

Preparation of Ethyl Acetate Extract of *Sphaeranthus indicus*

Dried flowering and fruiting heads of *Sphaeranthus indicus* (350 g) were pulverized. The powdered material was extracted using ethyl acetate (3 L) by stirring at 60° C. for 3 hrs. The extract was filtered under vacuum. This extraction process was repeated two more times. The extracts were combined and concentrated.

Yield: 19 g (9.5% w/w).

EXAMPLE 3

Preparation of Aqueous Extract of *Sphaeranthus indicus*

Dried flowering and fruiting heads of *Sphaeranthus indicus* (200 g) were pulverized. The powdered material was extracted using water (1.2 L) by stirring at 80° C.-90° C. for 3 hrs. The extract was filtered under vacuum. This extraction process was repeated. The extracts were combined and concentrated to remove water. Further, the crude extract was dried by freeze drying.

Yield: 21 g (10.5% w/w).

EXAMPLE 4

Isolation of 3a-hydroxy-5a,9-dimethyl-3-methylene-3a,4,5,5a,6,7,8,9b-octa hydro-3H-naphtho[1,2-b]furan-2-one (compound 1).

The methanol extract (32 g), prepared by the method described in example 1, was purified by column chromatography (silica gel, methanol in chloroform). Final purification was achieved by preparative HPLC (silica column, hexane:isopropanol, 95:5) to obtain the title compound.

1H NMR (CDCl$_3$, 500 MHz): δ1.085 (3H, CH$_3$), 4.997 (1H, s), 5.801 (1H, s), 6.270 (1H, s); MS: m/e (ES) 248 (M+).

Compound was characterized by comparing the obtained spectral data with the reported literature (Indian Journal of Chemistry, Vol. 25B, 233-238, (1986); J. Chem. Soc. Perkin Trans. 1:(2), 157-160, (1988); J. Chem. Research (M), 0501-0509, 1989).

Pharmacological Results

The efficacy of the present plant extracts, compounds isolated by purification of the said extract and formulations, in inhibiting the activity of TNF-α and interleukins (IL-1, IL-6, and IL-8) was determined by a number of pharmacological assays, well known in the art and described below.

In Vitro Screening to Identify Inhibitors of TNF-α

EXAMPLE 5

Primary Screening—Human Peripheral Blood Mononuclear Cells (hPBMCs).

TNF-α production by lipopolysaccharides (LPS) in hPBMCs was measured according to the method described by Jansky, L. et al (Physiol. Res. 52: 593-598, (2003)). Blood was collected from healthy donors into Potassium EDTA vacutainer tubes (BD vacutainer). The PBMCs were isolated using gradient centrifugation in Histopaque-1077 solution (Sigma). Isolated PBMCs were suspended in RPMI 1640 culture medium (Gibco BRL, Pasley, UK) containing 10% fetal bovine serum (FBS) (Hyclone, Utah, USA), 100 U/ml penicillin (Sigma Chemical Co. St Louis, Mo.) and 100 µg/ml streptomycin (Sigma Chemical Co. St Louis, Mo.). The cell concentration was adjusted to 1×10$^6$ cells/ml. The viability as determined by trypan blue dye exclusion was uniformly ≧98%. The cell suspension (100 µl) was added to the wells of a 96-well culture plate. Following cell plating, 79 µl of the culture medium and 1 µl of eight different concentrations of the test samples (final concentration 0.03, 0.1, 0.3, 1, 3, 10, 30, 100 µg/ml) dissolved in DMSO (dimethylsulfoxide, Sigma, Missouri, USA) were added to the cells. The final concentration of DMSO was adjusted to 0.5%. The vehicle (0.5% DMSO) was used as control. Rolipram (100, 300 µM) was used as a standard. The plates were incubated for 30 min at 37° C. in an atmosphere of 5% CO$_2$. Finally, 20 µl (10 µg/ml) per well of LPS, (*Escherichia coli* 0127:B8, Sigma Chemical Co., St. Louis, Mo.) was added, for a final concentration of 1 µg/ml. The plates were incubated at 37° C. for 5 h in an atmosphere of 5% CO$_2$. To assess the cytotoxic effect of the plant extracts, the cellular viability test was performed using MTS (3-(4,5-dimethylthiazol-2-yl)-5-(3-carboxymethoxyphenyl)-2-(4-sulfonyl)-2H-tetrazolium) reagent after 5 h of incubation. Supernatants were harvested and assayed for TNF-α by ELISA as described by the manufacturer (OptiEIA ELISA sets, BD Biosciences, Pharmingen). The % inhibition was recorded. Percent cytotoxicity of the test samples compared to control was evaluated.

The results are summarized in table 1.

TABLE 1

TNF-α inhibition in human peripheral blood mononuclear cells

| Sample | Concn. (µg/ml) | % Inhibition of TNF | % Toxicity at 5 h |
|---|---|---|---|
| Extract of example 1 | 0.1 | 0.0 | 0 |
| | 1 | 14.0 | 0 |
| | 10 | 96.0 | 7 |
| | 100 | 97.0 | 0 |
| Extract of example 2 | 0.1 | 0.0 | 20 |
| | 1 | 34.0 | 13 |
| | 10 | 97.0 | 22 |
| | 100 | 97.0 | 8 |

TABLE 1-continued

TNF-α inhibition in human peripheral blood mononuclear cells

| Sample | Concn. (μg/ml) | % Inhibition of TNF | % Toxicity at 5 h |
|---|---|---|---|
| Extract of example 3 | 0.1 | 0.0 | 0 |
|  | 1 | 0.0 | 11 |
|  | 10 | 4.0 | 0 |
|  | 100 | 96.0 | 0 |
| Rolipram (μM) | 100 | 84.0 | 2 |
|  | 300 | 90.0 | 21 |

EXAMPLE 6

Effect on Proinflammatory Cytokines Released by LPS-Stimulated hPBMCs

The effect of the plant extract on the proinflammatory cytokines: TNF-α, interleukin-1β (IL-1β), interleukin-6 (IL-6) and interleukin-8 (IL-8) was measured using the supernatants generated in the primary screening assay. The levels of these cytokines were estimated by ELISA as described by the manufacturer. (OptiEIA ELISA sets, BD Biosciences, Pharmingen). The 50% inhibitory concentration ($IC_{50}$) values were calculated by a nonlinear regression method using GraphPad software (Prism 3.03).

TABLE 2

Effect of the extract of example 1, on the proinflammatory cytokines

| Sr. No. | Pro-inflammatory Cytokines | Extract of example 1, $IC_{50}$ μg/ml, (hPBMC) |
|---|---|---|
| 01 | TNF-α | 5.1 |
| 02 | IL 1β | 4.9 |
| 03 | IL-6 | 26.8 |
| 04 | IL-8 | 31.0 |

Conclusion: Extract of example 1 was found to inhibit proinflammatory cytokines (TNF-α, IL-1β, IL-6 and IL-8) released by LPS-stimulated hPBMCs.

EXAMPLE 7

Effect of Compound 1, on Proinflammatory Cytokines Released by LPS-stimulated hPBMCs Compound 1 was obtained by using procedure of example 4. The bioactivity evaluation was done as per procedure of example 6.

The effect of the Compound 1, on the proinflammatory cytokines: TNF-α interleukin-1β (IL-1β), interleukin-6 (IL-6) and interleukin-8 (IL-8) was measured using the supernatants generated in the primary screening assay. The levels of these cytokines were estimated by ELISA as described by the manufacturer. (OptiEIA ELISA sets, BD Biosciences, Pharmingen). The 50% inhibitory concentration ($IC_{50}$) values were calculated by a nonlinear regression method using GraphPad software (Prism 3.03). The results are summarized in table 3.

TABLE 3

Effect of the Compound 1, on the proinflammatory cytokines

| Sr. No. | Pro-inflammatory Cytokines | Compound 1, $IC_{50}$ μM, (hPBMC) |
|---|---|---|
| 01 | TNF-α | 0.7 |
| 02 | IL 1β | 0.4 |
| 03 | IL-6 | 1.6 |
| 04 | IL-8 | 8.9 |

Conclusion: Compound 1 was found to inhibit proinflammatory cytokines (TNF-α, IL-1β, IL-6 and IL-8) released by LPS-stimulated hPBMCs.

EXAMPLE 8

Effect on Proinflammatory Cytokines Produced by Synovial Cells Obtained from a RA Patient Cytokine production by synovial cells obtained from a rheumatoid arthritis (RA) patient undergoing knee replacement surgery was measured according to the method described by Brennan, F. M. et al (The Lancet. July 29: 244-247, (1989)). The synovial membrane tissue was digested in DMEM (Gibco) containing 10% FBS, 100 U/ml penicillin and 100 μg/ml streptomycin, 4 mg/ml collagenase type I (Worthington), 1.5 μg/ml Dnase type I (Sigma) and 15 U/ml heparin and incubated at 37° C. for 3 hours. After incubation, the digested tissue was filtered through a 70-μm membrane and the cells washed 3 times in complete medium (DMEM with 10% FBS). The synovial cells were cultured at $1 \times 10^6$ cells/ml in presence/absence of the test sample for 10 hours. The supernatants were harvested by centrifugation and levels of the cytokines (TNF-α, IL-1β, IL-6, IL-8) measured by ELISA. To assess the cytotoxic effect of the plant extracts, the cellular viability test was performed using MTS reagent. The 50% inhibitory concentration ($IC_{50}$) values were calculated by a nonlinear regression method using GraphPad software (Prism 3.03).

Conclusion: Extract of example 1 was found to inhibit proinflammatory cytokines (TNF-α, IL-1β, IL-6 and IL-8) produced by synovial cells obtained from a RA patient.

EXAMPLE 9

Effect of compound 1 on proinflammatory cytokines produced by synovial cells obtained from a RA patient Effect on proinflammatory cytokines produced by synovial cells obtained from a RA patient was studied for compound 1 as described by procedure of example 8.

The results were summarized in table 4.

TABLE 4

Effect of compound 1, on proinflammatory cytokines produced by synovial cells.

| Sr. No. | Pro-inflammatory Cytokines | Compound 1, $IC_{50}$ (μM), Synovial |
|---|---|---|
| 01 | TNF-α | 0.8 |
| 03 | IL-6 | 1.4 |
| 04 | IL-8 | 10.9 |

Conclusion: Compound 1 was found to inhibit proinflammatory cytokines (TNF-α, IL-6 and IL-8) produced by synovial cells obtained from a RA patient.

EXAMPLE 10

Cell-ELISA for Adhesion Molecule Expression

The assay was designed on the basis of reference Transplantation, Vol 63 (5), 759-764, 1997 with modifications.

Cell Culture and Reagents:

Human Umbilical Vein Endothelial Cells (HUVECS) were obtained from Cascade Biologics and were maintained in M200 (Cascade Biologics, Portland, Oreg.) supplemented with low serum growth supplement (LSGS) at 37° C. in a 5% $CO_2$ incubator. U937 cells (ATCC, Manassas, Va.) were grown in the RPMI 1640 medium supplemented with 10% FBS (Hyclone, Logan, Utah). Recombinant human TNFα, antibodies to VCAM-1, ICAM-1, E-Selectin were obtained from R&D Systems and LPS was obtained from Sigma (St. Louis, Mo.).

Cell-ELISA for Adhesion Molecule Expression

HUVECs were plated at $7 \times 10^5$ cells/well in 96-well fibronectin-coated plates. The cells were stimulated with TNF-α (10 ng/ml) or LPS (1 µg/ml), 30 min after addition of test compound. After stimulation, cells (E-Selectin and ICAM-1) were fixed with paraformaldehyde in phosphate buffer saline (PBS). Non specific binding was blocked by 2% bovine serum albumin (BSA) in phosphate buffer saline (PBS) for 1 h, and the cells were incubated with primary antibody for 2 h. For detection of VCAM-1 the cells were blocked, incubated with primary antibody overnight, and then fixed. The cells were washed with 0.1% BSA in PBS, and incubated with peroxidase-conjugated antibody (Ab) to mouse immunoglobulin G (IgG) was added for 90 min. After washing, seven times, 3,3'5,5'-tetramethylbenzidine liquid substrate (TMB substrate) was added and the optical density of each well was determined at 450 nm using a microtitre plate reader (Spectramax, Molecular Devices, California). BAY 11-7082 [(E)-3-(4-methylphenylsulfonyl)-2-propenenitrile] was used as a standard and DMSO as vehicle control. Percent inhibition of the test sample compared to the control is evaluated. The 50% inhibitory concentration ($IC_{50}$) values for each sample compared to control are determined by a non-linear regression method. The results are summarized in table 5.

TABLE 5

Cell-ELISA for adhesion molecule expression for extract of example 1 and compound 1

| | Extract of example 1 $IC_{50}$ (µg/ml) | Compound 1 $IC_{50}$ (µM) |
|---|---|---|
| ICAM-1 | 7.6 | 0.52 |
| VCAM-1 | 6.4 | 0.4 |
| E-Selectin | 3.5 | 0.2 |

Conclusion: Extract of example 1 and compound 1 dose-dependently reduced TNF-α - induced surface expression of endothelial cell adhesion molecules such as ICAM-1, VCAM-1 and E-Selectin.

EXAMPLE 11

Adhesion of THP-1 Mononuclear Cells to HUVEC Monolayers

Adhesion studies were performed with the promonocytic cell line THP-1, which has been established as a useful model for monocytes in adhesion studies in Circ. Res., 97, 236-243, 2005, with modifications. THP-1 cells were washed twice with labeling medium (M200 plus LSGS). THP-1 cells ($6 \times 10^5$ cells per ml) were labeled with 10 µg/ml bis-carboxyethyl-carboxyfluorescein acetoxymethylester (a fluorescent probe, BCECF-AM; Sigma) for 30 min at RT. After quenching with 0.1% BSA, the pellet was resuspended in labeling medium. To evaluate monocyte adhesion, HUVEC monolayers treated with TNF-α (1 ng/ml) in the presence or absence of various concentrations of test sample. The media was removed, washed and labeled-THP-1-cells were added to the wells ($6 \times 10^4$ cells per well) and incubated for 10 minutes at RT in the dark. After co incubation, the wells were washed, filled with lysis buffer (0.1% Triton-X in 1.5 M Tris buffer) and incubated for 30 min. The fluorescence was measured using a fluorescent reader (PolarStar Optima, BMG Labtech) at an excitation peak of 485 nm and an emission peak of 520 nm. Values are means +SEM, representing fluorescent adhesion data. BAY 11-7082 [(E)-3-(4-methylphenylsulfonyl)-2-propenenitrile] was used as a standard and DMSO as vehicle control. The results are summarized in table 6.

TABLE 6

Adhesion of THP-1 mononuclear Cells to HUVEC monolayers for extract of example 1 and compound 1

| Sr. No. | Test Sample | Concentration | Fluorescence Intensity | Fold of control |
|---|---|---|---|---|
| 01 | Extract of example 1 | 1 (µg/ml) | 39768 | 23 |
| | | 3 (µg/ml) | 35302 | 21 |
| | | 10 (µg/ml) | 13183 | 6 |
| | | 30 (µg/ml) | 10236 | 5 |
| 02 | Compound 1 | 0.1 (µM) | 33421 | 13 |
| | | 0.3 (µM) | 34024 | 13 |
| | | 1 (µM) | 10195 | 4 |
| | | 3 (µM) | 5728 | 2 |
| 03 | BAY 11-7082 | 0.5 (µM) | 18442 | 10 |
| | | 1 (µM) | 14271 | 8 |
| 04 | Unstimulated DMSO Control | | 2544 | 1 |
| | Stimulated DMSO Control | | 30791 | 18 |

Conclusion: Extract of example 1 and compound 1 inhibited TNF-α stimulated monocytic THP-1 cell adhesion to HUVECs at 10 µg/ml and 1 µM respectively. Since these compounds inhibit the cell surface expression of adhesion molecules on HUVEC as well as monocyte adhesion to HUVECs, thereby they can hamper the leukocyte migration, which is a key event in chronic inflammatory diseases and could prove to be beneficial in numerous inflammatory disorders.

In Vivo Studies

All experiments were carried out in accordance with the guidelines of Committee for the Purpose of Control and Supervision of Experiments on Animals (CPCSEA) and with the approval of Institutional Animal Ethics Committee (IAEC).

EXAMPLE 12

Lipopolysaccharide (LPS)-Induced Tumor Necrosis Factor (TNF)-α Release in BALB/c Mice The protocol described by Fukuda T. et al (Eur. J. Pharmacol., 391: 317-320, (2000)) was followed. BALB/c mice were divided into groups of ten each. The test sample, suspended in Tween 80 and 0.5% carboxy methylcellulose (CMC), was orally (p.o.) administered to the mice. One hour later, LPS dissolved in sterile, pyrogen-free saline was administered i.p. at the dose of 1 mg/kg. The negative control group received saline as an i.p injection, while all other groups received LPS. Rolipram (30 mg/kg, p.o.) was used as the standard drug. One and a half hours later, under urethane anaesthesia (1.5 g/kg, i.p.) blood was collected from the abdominal artery using a 1 ml syringe flushed with heparin (500 IU/ml). Heparin (5 µl) was used as an anticoagulant in the blood collection tubes. Plasma was separated by centrifugation at 10000 rpm at room temperature, aliquoted and stored at −70° C. until analysis. TNF-α levels in the blood samples were assayed using ELISA and percent inhibition of TNF-α release compared to the control group was calculated. The results are summarized in table 7.

TABLE 7

Lipopolysaccharide (LPS)-induced Tumor Necrosis Factor (TNF)-α release in BALB/c mice for extract of example 1 and for compound 1.

| Sr. No. | Test sample | Dose mg/kg | % inhibition |
|---|---|---|---|
| 01 | Extract of example 1 | 100 | 43.21 ± 14.52 |
| 02 | Compound 1 | 10 | 28.69 ± 13.71 |
|  |  | 30 | 39.98 ± 10.32 |
|  |  | 100 | 87.10 ± 3.67 |

Conclusion: The extract of example 1 and compound 1, inhibit TNF-α release in BALB/c mice.

EXAMPLE 13

Collagen-induced Arthritis (CIA) in DBA/1J Mice

Male DBA/1J mice, aged 8-10 weeks, were immunized with 200 μg Collagen Type II as an emulsion in Freund's Complete Adjuvant, by an intradermal injection at the base of the tail. Twenty-one days later, the mice were administered a booster shot of 100 μg Collagen Type II. A set of naïve mice was also maintained alongside.

From Day 23 onwards, the mice were assessed for the onset of rheumatoid arthritis using the Articular Index as a parameter. Mice with a minimum hind paw score of 2 were inducted into the study. Extract of example 1 was administered at a dose of 400 mpk (Milligram per kilogram body weight) by oral route twice daily for 12 days. Compound 1 was administered at a dose of 50 mpk and 100 mpk. by oral route twice daily for 12 days. Enbrel (3 mg/kg) was used as a standard and was given subcutaneous once daily. Paw volume and articular index were recorded daily. The data was analysed for statistical significance.

On termination of the experiment the paws of the mice were processed for histopathological evaluation.

The data for reduction in paw thickness and reduction in articular index summarized in table 8.

TABLE 8

Efficacy of extract example 1 and compound 1 in CIA model

| Test sample | Dose mg/kg | Parameters CIA | |
|---|---|---|---|
| | | Reduction in paw thickness | Reduction in articular index |
| Extract of example 1 | 400 | Statistically significant over control at 0.01 level of significance | Statistically significant over control between 0.05 and 0.06 level of significance. |
| Compound 1 | 50 | Statistically significant over control at 0.05 level of significance | Statistically significant over control at 0.05 level of significance |
|  | 100 | Statistically significant over control at 0.01 level of significance | Statistically significant over control at 0.01 level of significance |

Histopathological Analysis:

Beneficial effect of extract of example 1 and compound 1 on pathology of arthritic (CIA) DBA/1J mice was evaluated. Microscopy was carried out after Hematoxylin and Eosin staining as well as Safranin O staining of synovial joints. Histopathological analysis showed that both extract of example 1 and compound 1 exerted beneficial effects in terms of reducing cartilage destruction, bone destruction and synovitis as compared to vehicle treated group.

Conclusion: Both extract of example 1 and compound 1 exerted beneficial effects in CIA model of arthritis

EXAMPLE 14

In Vivo Experiment

Dextran Sodium Sulphate (DSS)-induced Murine Model of Acute Colitis

The efficacy of test compounds on the gross pathology of colitis and proinflammatory mediators was studied by the method described in references, (Am. J. Physiol. Gastrointest Liver Physiol. 284: G138-144, (2003); Digestive Diseases Sciences, November; 52 (11): 2993-8, (2007)); with modifications, the disclosure of which is incorporated by reference for the teaching of the assay.

General procedure: C57BL/6J mice (6 weeks of age, weighing 18-22 g) were obtained from Jackson Laboratories (Bar Harbor, Me., USA) and were housed in individually ventilated cage (IVC) system. Colitis was induced in mice by replacing drinking water with 3% (wt/vol) DSS (MW 35-50 kDa; ICN Biomedicals, Aurora, Ohio, USA) in water ad libitum. DSS-induced Colitis was assessed by macroscopic and histological analyses of the colon. To probe the efficacy of test compounds, a group of mice was given oral administration of extract of example 1 (400 mg/kg; or 800 mg/kg) either intermittently or once daily in prophylatic mode or therapeutic treatment mode. In an experiment, groups of mice received oral administration of prednisolone (5 mg/kg), (Sigma Aldrich; St. Louis, Mo., USA), or dexamethasone (5 mg/kg) (Sigma Aldrich), or i.p. injections of infliximab (15 mg/kg), (Centocor; Horsham, Pa., USA).

Evaluation: DSS-induction of colitis was manifested with increase in clinical disease activity index associated with weight loss, diarrhea and presence of blood in feces. DSS-induced colitis was assessed by macroscopic and histological analyses of the colon.

Macroscopic analysis: At the end of DSS treatment period, mice were humanely euthanized with 15% urethane (i.p.). The whole colon (i.e., including ceacum, proximal colon and distal colon) was excised. The colon was macrosopically assessed by determining (a) the presence or absence of blood and (b) the longitudinal length.

Disease Activity Index: Various features were scored as delineated in the table 9. Disease activity index was the sum of scores of all features.

TABLE 9

Scoring criteria for various features

| Feature Scored | Score | Description |
|---|---|---|
| % Weight Loss | 0 | No Change/Increase |
|  | 1 | 0-5% Reduction |
|  | 2 | 5-10% Reduction |
|  | 3 | 10-15% Reduction |
|  | 4 | 15-20% Reduction |
| Rectal Bleeding | 0 | Absent |
|  | 1 | Slightly present |
|  | 2 | Heavy |

TABLE 9-continued

Scoring criteria for various features

| Feature Scored | Score | Description |
|---|---|---|
| Stool Consistency | 0 | Normal |
|  | 1 | Slightly loose |
|  | 2 | Loose |
|  | 3 | Diarrhoea |
| Blood in Colon | 0 | Absent |
|  | 1 | Slightly present |
|  | 2 | Markedly present |

Disease activity index = sum of scores of all features

Histological analysis: Colon biopsies from anterior, medial and distal part were collected and fixed in neutral buffered formalin (NBF). Paraffin embedded sections (5µ thickness) of the colon specimens were stained with Mayer's hematoxyllin (Sigma) and Eosin (Loba Chemie) and were graded by a blinded investigator. Histopathological scoring was based on presence of inflammatory cells, extent of crypt damage, erosions and over all architectural damage, each scored on a scale of 0 to 3 (Clin. Exp. Immunol, 114, 385-391, (1998)). Sections were scored for each feature separately and the sum of the scores was the final histopathological scoring for individual colon specimen. Histological assessment of disease activity was carried out by comparing the group mean histopathological score.

(A) Extract of Example 1, Fed Coincident with DSS Treatment

A group of 6 mice was given DSS solution from day 1 to 10. As a control for DSS treatment, a group of 6 mice was given regular drinking water from day 1 to 10 (normal mice). Separate groups of mice (6 mice per group) were given DSS solution from day 1 to 10 and received daily oral administration of either extract of example 1 (400 mg/kg) or prednisolone (5 mg/kg, standard, prednisolone administration started simultaneously with DSS treatment). All mice were sacrificed after day 10 and macroscopic and histological analysis of the colon was performed.

DSS-induction of colitis was manifested with increase in clinical disease activity index associated with weight loss, presence of rectal bleeding and stool consistency. DSS treatment also reduced the colon length.

Figure 1:
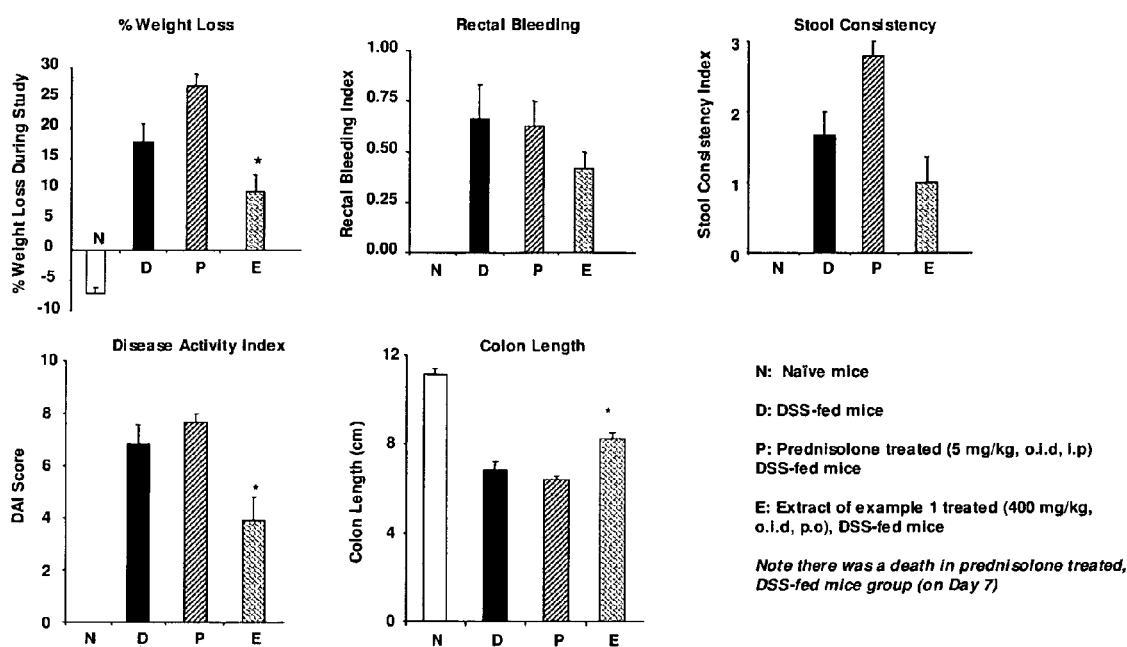
FIG. 1: Effect of extract of example 1 (fed coincident with DSS treatment) in C57BL/6J mice.

Extract of example 1, (400 mg/kg) fed coincident with DSS treatment, significantly inhibited the DSS-induced weight loss, rectal bleeding, improved stool consistency, decreased disease activity index and reduced the colon length. The results are indicated in FIG. 1.

Macroscopic observations revealed the consistent presence of blood throughout the colon of DSS mice. The appearance of blood was distinctly less frequent in case of DSS-mice which were fed with extract of example 1.

Colonic tissue sections from DSS mice, revealed severe inflammation, characterized by presence of edema, distinct inflammatory cellular infiltrate, extensive damage to mucosa and epithelium, along with crypt destruction. Tissue sections for the test mice, which were fed with extract of example 1 revealed significant attenuation in inflammation, characterized by suppression of edema, reduction in inflammatory cellular infiltrate, and pronounced protection against epithelium and crypt damage as indicated in FIG. 2.

Conclusion: Extract of example 1, fed coincident with DSS treatment, significantly inhibited DSS-induced macroscopic and histological abnormalities in the colon.

(B) Extract of Example 1, Fed Intermittently after DSS Treatment had Started

The effects of extract of example 1 (400 mg/kg), fed intermittently, after DSS treatment had started, were studied. In this set of experiments, a group of 6 mice was given DSS solution from day 1 to 10. As a control for DSS treatment, a group of 6 mice was given regular drinking water from day 1 to 10 (normal mice). Separate groups of mice (6 mice per group) were given DSS solution from day 1 to 10 and received oral administration of extract of example 1 (400 mg/kg) only on day 3, day 6 and day 10. Prednisolone (5 mg/kg) was used as a standard. All mice were sacrificed after day 10 and macroscopic and histological analysis of the colon was performed.

Extract of example 1, fed intermittently after DSS treatment had started, improved stool consistency, significantly reduced DSS induced disease activity index, and distinctly reduced colon length. The hemoglobin levels of DSS mice, fed with extract of example 1, were significantly higher as compared to that of DSS-treated mice. The results are indicated in FIG. 3.

Conclusion: Extract of example 1, fed intermittently after DSS treatment had started, significantly inhibited DSS-induced macroscopic and histological abnormalities in the colon.

(C) Extract of Example 1, Fed after DSS-induced Disease Expression was Evident

The efficacy of extract of example 1, fed after DSS-induced disease expression was evident, was studied. In this set of experiments, a group of 6 mice was given DSS solution from day 1 until death. (i.e. all animals in this group were dead). As a control, a group of 6 mice was fed regular drinking water. To probe the efficacy of extract of example 1, a group of 6 mice were given DSS solution from day 1 onwards and were fed extract of example 1 (800 mg/kg) from day 5 onwards up to day 30. a separate group of mice were given DSS solution from day 1 onwards and injected with infliximab (15 mg/kg) from day 5 onwards till death. (i.e. all animals in this group were dead). The change in body weight was observed.

Extract of example 1 was significantly efficacious in preventing DSS-induced weight loss. The results are indicated in FIG. 4A.

Extract of example 1 enhanced survival of mice against DSS-induced colitic death (50% survival at the end of 30 day). The results are indicated in FIG. 4B.

Conclusion: Extract of example 1 (800 mg/kg), fed after DSS-induced disease expression was evident, prevented weight loss and improved survival and protected against DSS-induced colitic death.

EXAMPLE 15

Atherosclerosis Model of High Fat-fed Hyperlipidemic Hamsters

The treatment effects of the extract of example 1 on prevention of aortic lesion were determined by using atherosclerosis model of high fat-fed hyperlipidemic hamster.

Details of animals used: Male Golden Syrian Hamsters, which were 7-8 weeks old and weighed approximately 100 g to 120 g, were used for the experiment.

Hamsters were randomly selected for treatment group placement. Animals were earmarked using a paint marker. Animals were separated and housed in groups of three in appropriately sized solid-bottom cages. Room lighting conditions were adjusted to 12 hour light and 12 hour dark cycle. During the acclimation period the diet was Purina 5001 (Research Diets, Inc. New Brunswick, N.J., USA). A high-fat diet consisting of Purina 5001 plus 10% coconut oil, 10% corn oil, 0.5% cholesterol, and 5% fructose was administered beginning on day 1 and continued throughout the duration of study. Hamsters were provided purified tap water throughout the study.

For pretreatment lipid values, animals were bled by retro-orbital puncture following an 18-hour fast and ~1 ml of blood was collected in a 3 ml Vacutainer® tube containing $K_3$ EDTA. Each blood sample was centrifuged (4000 rpm, 20 min, 4° C. using an Eppendorf C5804R) and the plasma separated and was analyzed for determination of triglyceride (TG), total cholesterol, high density cholesterol (HDL) and low density cholesterol (LDL).

Preparation of dosing solution: The extract of example 1 was dissolved in vehicle [CMC (0.5%)/Tween 80 (2%)] for 200 mpk (5 ml/kg BW) dosing. The resulting solution was a fine suspension after 12-15 minutes gentle sonication. Aliquots were prepared (~2.3 ml/vial) and stored in a freezer and were used daily.

All groups of animals were dosed orally either with vehicle or with extract of example 1 (200 mpk) for 58 days. Fenofibrate (100 mpk) was used as standard.

Animals were divided into three groups as indicated.

| Group | Dose | Hamsters | Days on Diet | N |
|---|---|---|---|---|
| Vehicle | | 1-12 | 60 | 12 |
| Fenofibrate | 100 mpk | 13-24 | 60 | 12 |
| Extract of example 1 | 200 mpk | 24-36 | 60 | 12 |

On day 58, following the 16-18 hour fasting period, animals were bled by retro-orbital puncture and ~1 ml of blood was collected in a 3 ml Vacutainer® tube containing $K_3$ EDTA. Each blood sample was centrifuged (4000 rpm, 20 min, 4° C. using an Eppendorf C5804R) and the plasma sample was analyzed for TG, total cholesterol, HDL and LDL.

The results are summarized in table 10.

TABLE 10

Percentage change in plasma triglycerides level in hyperlipidemic hamsters.

| Test Sample | Mean | SEM | % Change |
|---|---|---|---|
| Vehicle | 2321.3 | 451.0 | |
| Fenofibrate | 449.2 | 244.4 | −81% |
| Extract of example 1 | 1748.0 | 392.0 | −25% |

The results are indicated in FIG. 5A.

Necropsy: On day 59, the animals were fasted for 4 h and euthanized under carbon dioxide and plasma samples were collected via cardiac puncture for lipid profiling and other analyses. For perfusion, their thorax was opened and vasculature perfused first with heparinized saline (40 units/ml) for 2 minutes followed by 10% formalin for 8 minutes. The heart, aortic arch, thoracic and abdominal aorta up to femoral bifurcation were removed and placed in 10% formalin for en face lesion quantification.

En face analysis: Connective fascia and adventia surrounding the thoracic aorta were removed as much as possible. The abdominal aorta and renal arteries were exposed and cleaned up to the iliac bifurcation. Aortic arch was exposed from the surrounding tissues. The entire aorta from heart to iliac bifurcation was removed and placed in 10% neutral buffered formalin. Aorta was cut open longitudinally with lumen facing up and pinned down on a black wax plate followed by rinsing aorta briefly in 70% ethanol (2-3 times). The aorta was immersed in Oil Red-O staining solution for 5 min followed by de-staining in 70% ethanol for 5 minutes. Quantitation was performed using a Nikon SMZ-U microscope with an Optronics Camera head recording the photographs. Imaging was done using B Q Nova Prime software (BIOQUANT Image Analysis Corporation). Quantitation was done based on percentage lesion per area.

The results for atherosclerosis progression in hyperlipidemic hamsters are summarised in table 11.

TABLE 11

Percentage change in atherosclerosis progression in hyperlipidemic hamsters

| | Vehicle | Fenofibrate | Extract of example 1 |
|---|---|---|---|
| Mean | 0.5025 | 0.0834 | 0.2736 |
| STD | 0.2151 | 0.1131 | 0.1482 |
| SEM | 0.06487 | 0.03577 | 0.04686 |
| % Change | | −84 | −45 |

Atherosclerosis progression in hyperlipidemic hamsters is indicated in FIG. 5B.

Conclusion: Extract of example 1 lowered plasma triglycerides in hyperlipidemic hamsters. Extract of example 1 also inhibited atherosclerosis progression in hyperlipidemic hamsters. No change in body weight and no change in levels of cholesterol, HDL, and LDL were observed for hyperlipidemic hamsters on treatment with extract of example 1.

Toxicity Studies

EXAMPLE 16

Acute Oral Toxicity

Extract of example 1 was tested for acute oral toxicity to Sprague Dawley rats in compliance with the guidelines laid down in "Schedule Y" of the Drugs and Cosmetics Act, 1940. (India)

The extract of example 1, suspended in 0.5% Tween 80 in water, was administered orally by gavage as a single dose to a group of five male and five female rats at the maximum practicable dose of 2000 mg/kg body weight. The animals were observed for mortality and signs of intoxication for a period of 14 days post-dosing and their body weights were also recorded. Necropsy was performed on all rats at termination of the study.

Conclusion: In the present study, single oral administration of extract of example 1 to Sprague Dawley rats at the maximum practicable dose of 2000 mg/kg, did not cause any mortality in the treated rats.

The median lethal dose ($LD_{50}$) of extract of example 1 after oral administration as a single dose in Sprague Dawley rats, both male and female, was found to be more than 2000 mg/kg body weight.

EXAMPLE 17

Subacute Oral Toxicity

Subacute oral toxicity (28 Day) study of extract of example 1 in Sprague Dawley rats was performed in compliance with the guidelines laid down in "Schedule Y" of the Drugs and Cosmetics Act, 1940. (India)

Groups of six male and six female Sprague Dawley rats were administered daily doses of 0, 250, 500 or 1000 mg/kg body weight of extract of example 1 by oral gavage for 28 days and were sacrificed on day 29 to evaluate its toxicity. The rats were examined daily for signs of toxicity. Body weight and food consumption for individual rats were recorded during the experimental period along with all incidences of mortality and signs of ill health. Laboratory investigations were performed on blood at termination of the study.

All animals, when sacrificed terminally, were subjected to a complete necropsy and weights of certain organs were recorded. Histopathological evaluation was carried out on all protocol-listed tissues in all animals from control and high dosage groups.

All animals receiving the extract of example 1 at and up to the dose of 1000 mg/kg survived through the period of treatment. No clinical signs of toxicity were observed in any of the treated animals. The data on the body weight gain and food intake indicated no adverse effect due to the test article at and up to the dose of 1000 mg/kg.

Conclusion: Based on the findings of this study the no observable adverse effect level (NOAEL) of extract of example 1 in rats, following oral administration for 28 days was found to be more than 1000 mg/kg body weight.

Formulations

EXAMPLE 18

Preparation of Capsule

General procedure: Ingredients 01 to 05 in a specified quantity were weighed and transferred into a suitable mixer. The contents were mixed well and ingredients 09, 10 & 11 were added and the mixing was continued. To this blend ingredients 06, 07 & 08 were added and the mass was mixed for 30-45 minutes. The blend was passed through 40 mesh sieve, and was used for filling in capsules.

TABLE 12

Capsule formulation of *Sphaeranthus indicus*
Each capsule contains

| SR. NO. | INGREDIENT | QUANTITY % W/W |
|---|---|---|
| 01 | Extract of Example 1 | 69.72 |
| 02 | Sodium methyl paraben | 0.39 |
| 03 | Sodium propyl paraben | 0.13 |
| 04 | Bromerol | 0.18 |
| 05 | Sodium benzoate | 0.39 |
| 06 | Talcum | 2.61 |
| 07 | Magnesium stearate | 1.74 |
| 08 | Aerosil | 0.87 |
| 09 | Sodium starch glycolate | 2.18 |
| 10 | Lactose | 8.72 |
| 11 | Dibasic calcium phosphate | 13.07 |

EXAMPLE 19

Preparation of Tablet

General procedure: Ingredients 01 to 05 in a specified quantity were weighed and transferred into a suitable mixer. Ingredient 13 was added and the wet mass was mixed well. To it, ingredients 09, 10, 11 & 12 were added and mixing was continued till homogenized mass was obtained. This wet mass was passed through 16 mesh sieve and the wet granules were dried at 70° C.±5° C. Ingredients 06, 07 & 08 were added to the above granules and the mass mixed for 30-45 minutes. The blend was then passed through 40 mesh sieve and the tablets compressed using suitable punch.

TABLE 13

Tablet formulation of *Sphaeranthus indicus*
Each tablet contains

| SR. NO. | INGREDIENT | QUANTITY % W/W |
|---|---|---|
| 01 | Extract of example 1 | 66.53 |
| 02 | Sodium methyl paraben | 0.37 |
| 03 | Sodium propyl paraben | 0.12 |
| 04 | Bromerol | 0.17 |
| 05 | Sodium benzoate | 0.37 |
| 06 | Talcum | 2.50 |
| 07 | Magnesium stearate | 1.66 |
| 08 | Aerosil | 0.83 |
| 09 | Sodium starch glycolate | 2.50 |
| 10 | Lactose | 8.32 |
| 11 | Dibasic calcium phosphate | 12.47 |
| 12 | Starch | 4.16 |
| 13 | Isopropanol | * |

* for granulation only

EXAMPLE 20

Preparation of Syrup

General Procedure

Ingredient 01 was weighed and to it ingredient 15 was added under continuous stirring. To it were added weighed amounts of ingredients 03, 04, 05, 06, 08, 09, 10, 11, 12 and 14 with continuous stirring to dissolve. Ingredients 02 and 13 were weighed and dissolved in ingredient 07. To it purified water was added to adjust volume to 10 ml. The obtained solution was filtered through filter press/nylon cloth.

TABLE 14

Syrup formulation of *Sphaeranthus indicus*
Each 10 ml syrup contains

| SR. NO. | INGREDIENT | QUANTITY % W/W |
|---|---|---|
| 01 | Extract of Example 1 | 4 |
| 02 | Mentha piperita powder | 0.025 |
| 03 | Honey | 0.25 |
| 04 | Sugar | 50 |
| 05 | Sorbitol solution 70% | 5 |
| 06 | Liquid glucose | 10 |
| 07 | Propylene glycol | 5 |
| 08 | Citric acid monohydrate | 0.5 |
| 09 | Sodium methyl paraben | 0.2 |
| 10 | Sodium propyl paraben | 0.02 |
| 11 | Sodium benzoate | 0.2 |
| 12 | Bronopol | 0.02 |
| 13 | Cool mint 'S' flavour | 0.25 |
| 14 | Sugar caramel colour | 0.75 |
| 15 | Purified water | q.s to 10 ml |

EXAMPLE 21

Preparation of Cream Formulation

General Procedure

Ingredient 01 was weighed and suspended in ingredient 17. Ingredients 02 to 07 were melted. Ingredients 08, 09, 10, 11, 13 and 14 were weighed and mixed with portion of 18. Ingredient 12 was weighed and added to remaining portion of ingredient 18 and was mixed with ingredients 15 and 16. The contents of all stages were mixed at 55° C. and homogenized, allowed to cool and packed in a suitable tube.

TABLE 15

Cream Formulation of *Sphaeranthus indicus*
Each 100 g cream contains

| SR. NO. | INGREDIENT | QUANTITY % W/W |
|---|---|---|
| 01 | Extract of example 1 | 05.00 |
| 02 | Cetostearyl alcohol - 12.0 g | 12.00 |
| 03 | Cetomacragol - 1000 | 03.00 |
| 04 | Sorbitan mono-oleate | 02.00 |
| 05 | S.E. glycerol monostearate | 03.00 |
| 06 | Isopropyl myristate | 02.50 |
| 07 | Stearic acid | 02.50 |
| 08 | Sodium methyl paraben | 00.40 |
| 09 | Sodium propyl paraben | 00.08 |
| 10 | Phenoxy ethanol | 00.52 |
| 11 | Disodium EDTA | 00.02 |
| 12 | Carbomer - 940 | 00.75 |
| 13 | Sodium lauryl sulphate | 00.75 |
| 14 | Simethicone | 01.00 |
| 15 | Triethanolamine | 01.00 |
| 16 | Propylene glycol | 05.00 |
| 17 | Isopropanol | 10.00 |
| 18 | Water | 50.48 |

EXAMPLE 22

Preparation of Gel Formulation
General Procedure

Ingredient 01 was weighed and was suspended in ingredient 06. Ingredient 04 was dissolved in ingredient 07. Ingredients 05 and 08 were mixed. Ingredients 02 and 03 were mixed. The blend was mixed well and was packed in suitable tube.

TABLE 16

Gel formulation of *Sphaeranthus indicus*
Each 100 g gel contains

| SR. NO. | INGREDIENT | QUANTITY % W/W |
|---|---|---|
| 01 | Extract of example 1 | 05.00 |
| 02 | Butylated hydroxy toluene | 00.025 |
| 03 | Butylated hydroxy anisole | 00.025 |
| 04 | Carbopol - 940 | 02.95 |
| 05 | Polyethylene glycol - 400 | 30.00 |
| 06 | Isopropanol | 05.00 |
| 07 | Propylene glycol | 55.00 |
| 08 | Sorbitan mono oleate | 02.00 |

EXAMPLE 23

Preparation of Ointment Formulation
General Procedure

Ingredients 02 to 06 were weighed and melted in a suitable vessel. To this, ingredient 01 was added. Ingredients 07 and 08 were added to this blend. The contents were mixed well and packed in a suitable tube.

TABLE 17

Ointment formulation of *Sphaeranthus indicus*
Each 100 g ointment contains

| SR. NO. | INGREDIENT | QUANTITY % W/W |
|---|---|---|
| 01 | Extract of example 1 | 5.00 |
| 02 | White bees wax | 15.00 |
| 03 | Hard paraffin | 25.00 |
| 04 | Microcrystalline wax | 15.00 |
| 05 | White soft paraffin | 30.00 |
| 06 | Light liquid paraffin | 09.95 |
| 07 | Butylated hydroxy toluene | 0.025 |
| 08 | Butylated hydroxy anisole | 0.025 |

EXAMPLE 24

Preparation of Tablet
General Procedure

Ingredients 01 and 02 were weighed separately and sifted through 20 mesh and mixed. Ingredients 03 to 07 were weighed and sifted through 40 mesh. Ingredients 03, 04, 05 and 07 were mixed and to this mixture of ingredients 01 and 02 was added. To this blend ingredient 06 was added and mixed. Lubricated blend obtained was compressed with suitable machine tool.

TABLE 18

Tablet formulation of compound 1
Each tablet contains

| Sr. No. | Ingredients | Quantity % w/w |
|---|---|---|
| 01 | Compound 1 | 58.33 |
| 02 | Microcrystalline cellulose | 35.97 |
| 03 | Talc | 2.50 |
| 04 | Sodium starch glycolate | 1.60 |
| 05 | Colloidal silicon dioxide | 0.80 |
| 06 | Magnesium stearate | 0.50 |
| 07 | Colour quinoline yellow | 0.30 |

EXAMPLE 25

Preparation of Tablet
General Procedure

Ingredients 01 and 02 were weighed separately and sifted through 20 mesh. Ingredient 04 was dissolved in ingredient 08 with stirring. The above blend was granulated using binding solution. The wet mass was passed through suitable sieve. The sifted mass was dried at room temperature (25° C.) and then at about 40° C. Dried mass was sifted through suitable sieve. Ingredients 03, 05 and 07 were separately sifted through 40 mesh and mixed. To this dried mass was added and mixed. To this blend ingredient 06 was added and the lubricated blend was compressed with suitable machine tool.

TABLE 19

Tablet formulation of compound 1
Each tablet contains

| S. No. | Ingredients | Quantity % w/w |
|---|---|---|
| 01 | Compound 1 | 61.40 |
| 02 | Lactose monohydrate | 35.15 |
| 03 | Crosscarmulose sodium | 1.40 |
| 04 | Polyvinylpyrrolidone | 0.85 |
| 05 | Colloidal silicon dioxide | 0.35 |
| 06 | Magnesium stearate | 0.50 |
| 07 | Colour quinoline yellow | 0.35 |
| 08 | Isopropyl alcohol | Quantity sufficient |

EXAMPLE 26

Preparation of Capsule
General Procedure

Ingredients 01 and 02 were weighed separately and sifted through 20 mesh and mixed. Ingredient 03 was weighed and sifted through 40 mesh. All the ingredients were mixed and lubricated using ingredient 04. The blend was filled in empty hard gelatin capsule using suitable machine tools.

TABLE 20

Capsule formulation of compound 1
Each capsule contains

| Sr. No. | Ingredients | Quantity % w/w |
| --- | --- | --- |
| 01 | Compound 1 | 98.59 |
| 02 | Microcrystalline cellulose | 0.75 |
| 03 | Colloidal silicon dioxide | 0.47 |
| 04 | Magnesium stearate | 0.19 |

We claim:

1. A method of treating an inflammatory disorder comprising administering to a subject in need thereof a therapeutically effective amount of a composition comprising a therapeutically effective amount of an extract of flowering and fruiting heads of the plant, *Sphaeranthus indicus* as an active ingredient along with pharmaceutically acceptable carriers wherein the inflammatory disorder is selected from the group consisting of rheumatoid arthritis, juvenile rheumatoid arthritis, psoriatic arthritis, osteoarthritis, refractory rheumatoid arthritis, and chronic non-rheumatoid arthritis.

2. The method of claim 1, wherein the composition is formulated for oral administration.

3. The method of claim 1, wherein the composition is formulated for topical administration.

4. The method of claim 1, wherein the composition is formulated for transdermal administration.

5. The method of claim 1, wherein the inflammatory disorder is rheumatoid arthritis.

6. The method of claim 1, wherein the extract of *Sphaeranthus indicus* contains a bioactive marker.

7. The method of claim 6, wherein the bioactive marker contained in the extract of *Sphaeranthus indicus* is 3a-hydroxy-5a, 9-dimethyl-3-methylene-3a, 4,5,5a,6,7,8,9b-octahydro-3H-naphtho[1,2-b]furan-2-one (compound 1).

8. The method of claim 7, wherein the extract of *Sphaeranthus indicus* contains 2-9% of the said compound 1.

* * * * *

UNITED STATES PATENT AND TRADEMARK OFFICE
CERTIFICATE OF CORRECTION

PATENT NO. : 7,635,494 B2
APPLICATION NO. : 12/079853
DATED : December 22, 2009
INVENTOR(S) : Chauhan et al.

It is certified that error appears in the above-identified patent and that said Letters Patent is hereby corrected as shown below:

Title Page, Item (75) Inventors: Delete
Inventors "Ravindra Dattatraya GUPTE, Nilesh Madhukar DAGIA, Somesh SHARMA, Shruta Sudheer DADARKAR, Mahesh Gundaji JADHAV and Aditi Amol TANNU"

Signed and Sealed this

Twenty-third Day of March, 2010

David J. Kappos
*Director of the United States Patent and Trademark Office*